United States Patent
Stetson

(10) Patent No.: US 11,455,900 B2
(45) Date of Patent: Sep. 27, 2022

(54) SYSTEM AND METHOD FOR TEACHING A SURGICAL PROCEDURE

(71) Applicant: Surg Time, Inc., Burbank, CA (US)

(72) Inventor: William B. Stetson, Burbank, CA (US)

(73) Assignee: SURGTIME, INC., Burbank, CA (US)

( * ) Notice: Subject to any disclaimer, the term of this patent is extended or adjusted under 35 U.S.C. 154(b) by 270 days.

(21) Appl. No.: 16/801,619

(22) Filed: Feb. 26, 2020

(65) Prior Publication Data
US 2020/0273359 A1 Aug. 27, 2020

Related U.S. Application Data

(60) Provisional application No. 62/958,064, filed on Jan. 7, 2020, provisional application No. 62/810,838, filed on Feb. 26, 2019.

(51) Int. Cl.
| | |
|---|---|
| *G09B 5/06* | (2006.01) |
| *A61B 34/10* | (2016.01) |
| *G06F 3/16* | (2006.01) |
| *G10L 25/51* | (2013.01) |
| *H04L 65/611* | (2022.01) |
| *H04L 65/75* | (2022.01) |

(52) U.S. Cl.
CPC ............. *G09B 5/065* (2013.01); *A61B 34/10* (2016.02); *G06F 3/165* (2013.01); *G10L 25/51* (2013.01); *H04L 65/611* (2022.05); *H04L 65/762* (2022.05)

(58) Field of Classification Search
CPC ......... G09B 5/065; G06F 3/165; A61B 34/10; H04L 65/4076; H04L 65/602; H04L 65/611; H04L 65/762; H04L 65/403; G10L 25/51
See application file for complete search history.

(56) References Cited

U.S. PATENT DOCUMENTS

| | | | | |
|---|---|---|---|---|
| 9,298,884 | B1 * | 3/2016 | Ahmad | G06F 3/00 |
| 2007/0094052 | A1 * | 4/2007 | Blas | G16H 15/00 |
| | | | | 705/3 |
| 2016/0210411 | A1 * | 7/2016 | Mentis | G16H 30/20 |
| 2020/0162794 | A1 * | 5/2020 | Nishino | H04N 21/4882 |

* cited by examiner

*Primary Examiner* — Oschta I Montoya
(74) *Attorney, Agent, or Firm* — Lewis Roca Rothgerber Christie LLP

(57) ABSTRACT

A method of teaching a surgical procedure includes transmitting a first video, from a first location to a second location remote from the first location, of a surgeon in an operating room performing the surgical procedure on a patient with at least one surgical instrument. The method also includes transmitting a second video, from the first location to the second location, of the surgical instrument during the surgical procedure, annotating the second video with at least one annotation, and transmitting, from the first location to the second location, the at least one annotation overlaid on the second video.

20 Claims, 3 Drawing Sheets

SYSTEM AND METHOD FOR TEACHING A SURGICAL PROCEDURE

CROSS-REFERENCE TO RELATED APPLICATION(S)

The present application claims priority to and the benefit of U.S. Provisional Application No. 62/810,838, filed Feb. 26, 2019, and U.S. Provisional Application No. 62/958,064, filed Jan. 7, 2020, the entire contents of both of which are incorporated herein by reference.

BACKGROUND

1. Field

The present disclosure relates generally to systems and methods for teaching a surgical procedure to remotely located individuals.

2. Description of Related Art

Many surgical procedures, such as shoulder arthroscopy, require specialized training and expensive equipment, which are barriers to adoption of these surgical procedures in developing countries such as Haiti, Cuba, and Romania. As a result, the utilization of resources to teach these surgical procedures in developing countries is limited. For instance, in developing countries, arthroscopic surgical skills are not often emphasized in training programs and, in particular, shoulder arthroscopic skills may not be taught. Accordingly, less efficacious but more accessible treatment options are often chosen in developing countries. For instance, an individual suffering a shoulder dislocation may be treated non-operatively with immobilization even though the patient would benefit more from arthroscopic repair. As a result, patients in developing nations are more likely to have recurrent injuries, which will reduce their functional status and increase disability and time out of work.

Additionally, many surgical procedures, including arthroscopy, have traditionally been taught to residents or other surgeons through one-on-one in-person guided training in the operating room. When one-on-one in-person training is not available, simulators have been used to increase the availability of exposure to arthroscopy training. However, these simulators have significant limitations and cannot be definitively linked to improvement in arthroscopy skills in the operating room.

SUMMARY

The present disclosure is directed to various embodiments of a method of teaching a surgical procedure. In one embodiment, the method includes transmitting a first video, from a first location to a second location remote from the first location, of a surgeon in an operating room performing the surgical procedure on a patient with at least one surgical instrument, and transmitting a second video, from the first location to the second location, of the surgical instrument during the surgical procedure. The method also includes annotating the second video with at least one annotation, and transmitting, from the first location to the second location, the at least one annotation overlaid on the second video.

The first video may be an extracorporeal video of the surgeon and at least a portion of the patient, and the second video may be an intracorporeal video of the surgical instrument inside the patient.

Transmitting the first video, the second video, and the at least one annotation overlaid on the second video may be performed by transmitting a single video stream including the first video, the second video, and the at least one annotation overlaid on the second video.

The method may also include displaying the second video on a display in the operating room.

The method may further include displaying on the display in the operating room at least one annotation transmitted from the second location.

Annotating the second video may be performed with an input device connected to the display in the operating room, and the input device may be, for example, a mouse, a stylus, a keyboard, a touch screen, or combinations thereof.

The at least one annotation may include a shape, a symbol, a graphic, text, or combinations thereof.

The method may also include transmitting, from the first location to the second location, audio captured by a microphone in the operating room, and/or generating audio, from a speaker in the operating room, captured by a microphone at the second location.

Transmitting the first video may be performed synchronously with transmitting the second video, and transmitting the first video and the second video may be performed in real-time.

Annotating the second video may be performed by an individual other than the surgeon.

According to another embodiment of the present disclosure, the method of teaching a surgical procedure includes transmitting a first video stream, captured by a first video camera in an operating room, of a surgeon performing the surgical procedure with a least one surgical instrument, and transmitting a second video stream, captured by a second video camera in the operating room, of the at least one surgical instrument during the surgical procedure.

Transmitting the first video stream and the second video stream may be performed in real-time.

The method may also include displaying, on a display in the operating room, the second video stream, annotating, with an input device connected to the display, the second video stream with at least one annotation; and transmitting the at least one annotation overlaid on the second video stream.

The operating room and the remote device may be located in the same country or different countries.

The first video stream may include an extracorporeal view of the surgeon and at least a portion of the patient, and the second video stream may include an intracorporeal view of the surgical instrument inside the patient.

The present disclosure is also directed to various embodiments of a system for teaching a surgical procedure. In one embodiment, the system includes a first video camera in operating room configured to capture extracorporeal video of a surgeon performing the surgical procedure with at least one surgical instrument in the operating room, a second video camera in the operating room configured to capture intracorporeal video of the at least one surgical instrument inside the patient during the surgical procedure, a display in the operating room configured to display at least the intracorporeal video, an input device connected to the display, the input device configured to generate annotations overlaid on the intracorporeal video, and a network adapter configured to transmit the extracorporeal video of the surgeon, the intracorporeal video of the at least one surgical instrument, and the annotations overlaid on the intracorporeal video to a site remote from the operating room.

The system may also include a speaker connected to the network adapter in the operating room configured to generate audio in the operating room captured from the site remote, and a microphone connected to the network adapter in the operating room configured to transmit audio captured by the microphone to the remote site.

The input device may be a mouse, a stylus, a keyboard, a touch screen, or combinations thereof.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

BRIEF DESCRIPTION OF THE DRAWINGS

The features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

The present disclosure is directed to various embodiments of systems and methods for teaching a surgical procedure (e.g., a surgical operation, such as arthroscopic shoulder surgery) to one or more users located remote from the medical facility in which the surgical procedure is being performed. The systems and methods of the present disclosure include the transmission of live video of the surgical procedure on the patient, the medical professional, and surgical instruments utilized in the surgical procedure, as well as annotations such as text and/or graphics overlaid on one or more of the live videos, to the one or more remote users. The annotated live videos enable the medical personnel to teach various surgical procedures by, for example, highlighting certain anatomical structures at the surgical site, identifying various medical equipment utilized during the procedure, and/or explaining various techniques utilized during the surgical procedure. The systems and methods according to one or more embodiments of the present disclosure also include receiving audio from the one or more remote users and transmitting audio from the medical professional to the remote users, which enables the medical professional to converse with the remote users during the surgical procedure to answer questions posed by the remote user and to explain various techniques and/or equipment being utilized in the surgical procedure. Teaching surgical procedures to remote users utilizing the systems and methods of the present disclosure enables adoption of these surgical procedures on a global scale, including in developing nations that might otherwise adopt less efficacious treatment options.

Figure 1:
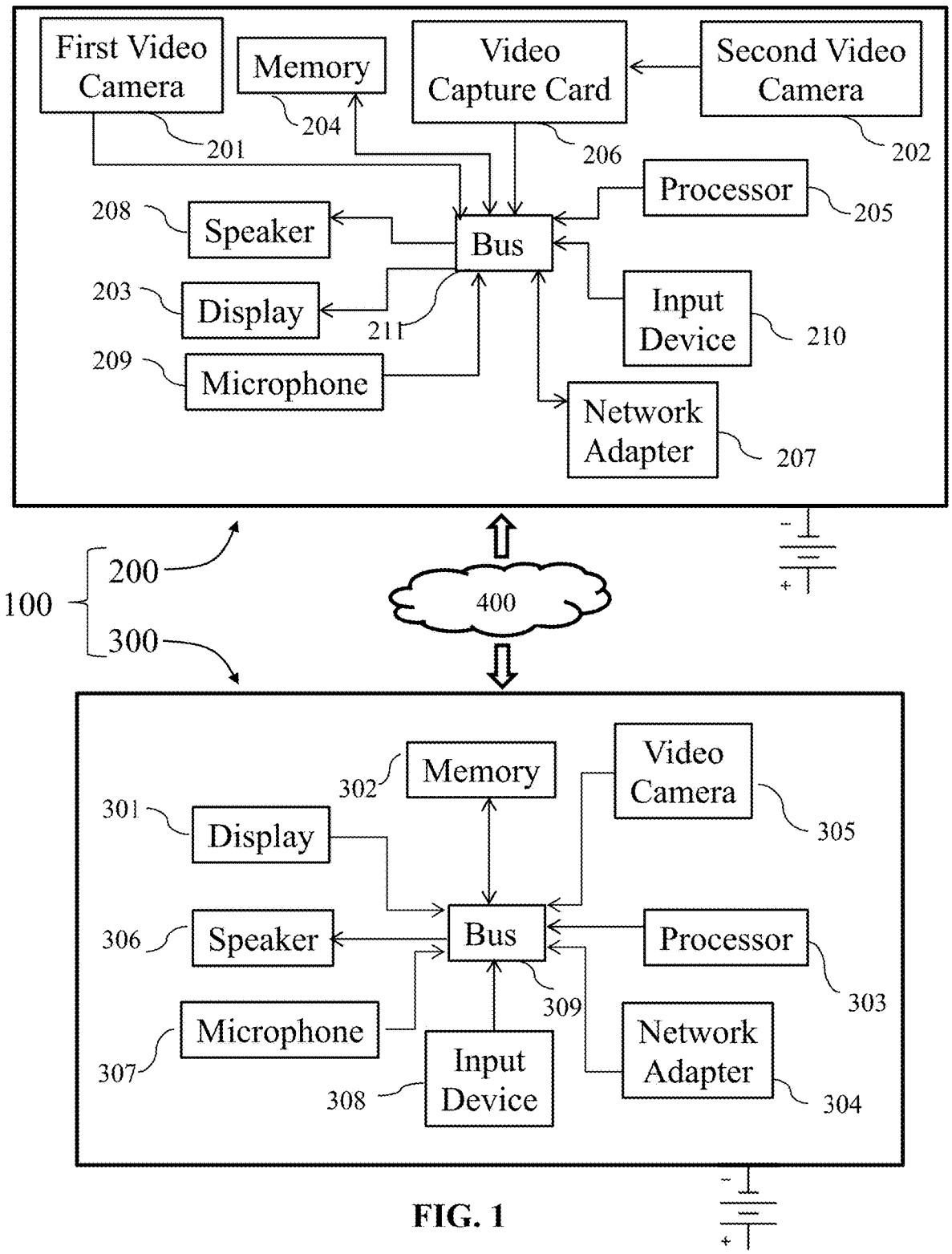
FIG. 1 is a schematic block diagram of a system for teaching a medical procedure according to one embodiment of the present disclosure.

FIG. 1 is a block diagram of a system 100 according to one embodiment of the present disclosure for teaching a surgical procedure to one or more remotely located individuals. In the illustrated embodiment, the system 100 includes a medical site system 200 configured to communicate with a remote site system 300 over a network 400. The network 400 may be a wired network or a wireless network depending, for instance, on the desired network reliability and/or the desired network connection speed between the medical site system 200 and the remote site system 300. The medical site system 200 is located in a medical facility where a medical professional will perform a surgical procedure on a patient, and the remote site system 300 is located where an individual (e.g., a trainee and/or other observers) will remotely observe the surgical procedure. In one or more embodiments, the remote site system 300 may be located in a developing country, such as Haiti, Cuba, or Romania, that historically lacked access to specialized medical equipment and/or medical training resources. Accordingly, in one or more embodiments, the medical site system 200 may be located domestically (e.g., in the United States) and the remote site system 300 may be located internationally (e.g., in a foreign country outside the United States). However, in one or more embodiments, the remote site system 300 may be located in the same country as the medical site system 200 (e.g., the remote site system 300 and the medical site system 200 may both be located domestically, such as in the United States).

In the illustrated embodiment, the medical site system 200 includes a first video camera 201, a second video camera 202, a display 203, a memory device 204 (e.g., persistent memory such as NAND flash memory), a processor 205, a video capture card 206, a network adapter 207, a speaker 208, a microphone 209, and an input device 210. In the illustrated embodiment, the first and second video cameras 201, 202, the display 203, the memory 204, the processor 205, the video capture card 206, the network adapter 207, the speaker 208, the microphone 209, and the input device 210 may communicate with each other over a system bus 211. In one or more embodiments, the memory 204, the processor 205, the video capture card 206, and the network adapter 207 may be embodied in a computer. In one or more embodiments, the memory 204, the processor 205, the video capture card 206, the network adapter 207, the first video camera 201, the display 203, the speaker 208, and the microphone 209 may be embodied in a computer.

The term "processor" is used herein to include any combination of hardware, firmware, and software, employed to process data or digital signals. The hardware of a processor may include, for example, application specific integrated circuits (ASICs), general purpose or special purpose central processors (CPUs), digital signal processors (DSPs), graphics processors (GPUs), and programmable logic devices such as field programmable gate arrays (FPGAs). In a processor, as used herein, each function is performed either by hardware configured, i.e., hard-wired, to perform that function, or by more general purpose hardware, such as a CPU, configured to execute instructions stored in a non-transitory storage medium. A processor may be fabricated on a single printed wiring board (PWB) or distributed over several interconnected PWBs. A processor may contain other processors; for example a processor may include two processors, an FPGA and a CPU, interconnected on a PWB.

In the illustrated embodiment, the remote site system 300 includes a display 301, a memory device 302 (e.g., persistent memory such as NAND flash memory), a processor 303, and a network adapter 304. In one or more embodiments, the remote site system 300 may also include a video camera 305, a speaker 306, a microphone 307, and an input device 308. In the illustrated embodiment, the display 301, the memory 302, the processor 303, the network adapter 304, the video camera 305, the speaker 306, the microphone 307, and the input device 308 may communicate with each other over a system bus 309. In one or more embodiments, the display 301, the memory 302, the processor 303, the network adapter 304, the video camera 305, the speaker 306, the microphone 307, and the input device 308 may be embodied in a computer.

The first video camera 201 of the medical site system 200 is positioned in the medical facility (e.g., an operating room at a hospital) such that the first video camera 201 is configured to capture real-time video of the medical professional performing a surgical procedure on the patient (e.g., the first video camera 201 is configured to capture real-time video of a surgeon performing surgery on the patient). In one embodiment, the first video camera 201 is configured to capture an exterior view of the medical professional and the patient (e.g., an exterior view of the arthroscopic surgeon and an exterior view of the patient's shoulder). Accordingly, in one or more embodiments, the first video camera 201 is configured (e.g., located) to capture extracorporeal video of the patient and the surgeon.

The second video camera 202 is configured to capture video of one or more medical instruments being utilized by the medical professional during the medical procedure. In one or more embodiments, depending on the nature of the medical procedure, the second video camera 202 may be configured to capture video inside the patient. That is, in one or more embodiments, the second video camera 202 is configured (e.g., located) to capture intracorporeal video of the patient at the site where the one or more medical instruments are being utilized by a medical professional during a medical procedure. For instance, in one or more embodiments in which the medical procedure being performed and taught is arthroscopic shoulder surgery, the second video camera 202 may be a surgical video camera inserted into the patient's shoulder proximate to the surgical site to capture live intracorporeal video of one or more of the surgical instruments utilized by the surgeon during the shoulder arthroscopy, such as suture anchors, a switching stick, cannula-trocar sets, a labral probe, a crochet hook, a knot pusher, tissue elevators, glenoid rasps, and/or a suture retriever.

The output (e.g., video stream) of the first video camera 201 and the output (e.g., video stream) of the second video camera 202 are each connected to the display 203 such that the display 203 of the medical site system 200 is configured to display the video captured by the first video camera 201 and the video captured by the second video camera 202. In the illustrated embodiment, the output of the second video camera 202 is connected to the display 203 via the video capture card 206, which enables the transmission of analog video captured from the second video camera 202 through a digital platform. In one or more embodiments, the system 200 is configured to display the video (e.g., the extracorporeal video stream) of the medical professional and the patient captured by the first video camera 201 synchronously or substantially synchronously with the video (e.g., the intracorporeal video stream) of the one or more surgical instruments captured by the second video camera 202. In one or more embodiments, the system 200 is configured to display, on the display 203, the video (e.g., the extracorporeal video stream) of the medical professional and the patient captured by the first video camera 201 and the video (e.g., the intracorporeal video stream) of the one or more surgical instruments captured by the second video camera 202 in real-time or substantially in real-time.

With continued reference to the embodiment illustrated in FIG. 1, the input device 210 is configured to enable a user to annotate the video captured by the first video camera 201 and/or annotate the video captured by the second video camera 202. The input device 210 may enable any suitable type or kind of annotations, such as, for instance, graphics (e.g., arrows or an oval) and text (e.g., words indicating various anatomical features of the patient, such as the head of the humerus, and/or the surgical technique being performed by the surgeon). The input device 210 may be any suitable type or kind of electronic device, such as, for instance, a mouse, a stylus, a keyboard, and/or a touch screen (i.e., a touch sensitive display).

The system 100 of the present disclosure also includes a video conferencing platform configured to enable the transmission of video and/or audio between the medical site system 200 and the remote site system 300. The video conferencing platform is accessible by both the medical site system 200 and the remote site system 300. In one or more embodiments, the video conferencing platform may be stored locally on the memory 204 of the medical site system 200 and the memory 302 of the remote site system 300, or the video conferencing platform may be stored on a remote server (i.e., the video conferencing server may be hosted in the "cloud") accessible by network adapters 207 and 304 of the medical site system 200 and the remote site system 300, respectively. The video conferencing platform is a software program that includes instructions, which, when executed by a processor, cause the processor to perform various functions. In one or more embodiments, the instructions cause the processor to read and/or write data to and from the memory, and to send commands to, and receive data from, various other components of the system, including the first camera, the second camera, the display, and the network adapter.

In one embodiment, the video conferencing platform has instructions stored therein, which, when executed by the processor 205 of the medical site system 200, cause the display 203 of the medical site system 200 to display the video of the medical professional and the patient captured by the first video camera 201 and to display the video of the one or more surgical instruments utilized in the surgical procedure captured by the second video camera 202. In one or more embodiments, the video of the medical professional and the patient and the video of the one or more surgical instruments may be displayed in separate windows on the same display 203, the video of the medical professional and the patient and the video of the one or more surgical instruments may be displayed in the same window on the same display 203, or the video of the medical professional and the patient and the video of the one or more surgical instruments may be displayed on separate displays 203.

The video conferencing platform includes instructions therein, which, when executed by the processor 205 of the medical site system 200, cause the processor 205 to overlay the annotations, input via the input device 210, on the video captured by the first video camera 201 and/or the second video camera 202 and to display the videos with the overlaid annotations on the display 203.

The video conferencing platform also includes instructions therein, which, when executed by the processor 205 of the medical site system 200, cause the medical site system 200 to transmit, via the network adapter 207, the videos captured by the first and second video cameras 201 and 202 with the overlaid annotations to the remote site system 300.

Figure 3A:
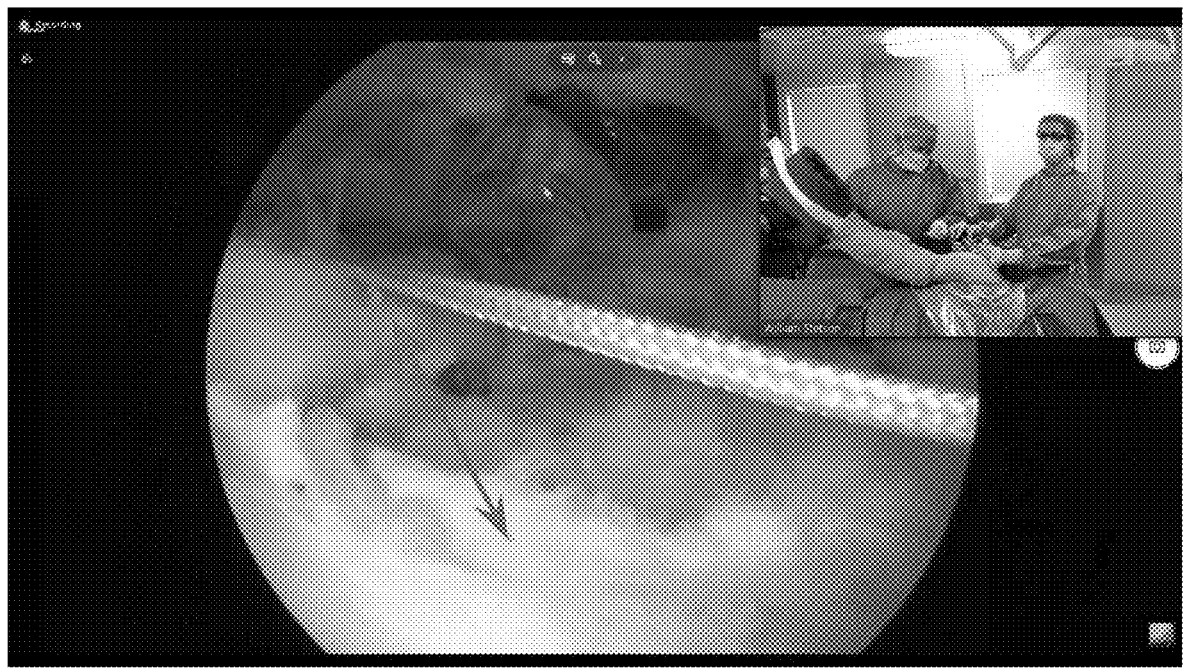
FIGS. 3A-3B illustrate videos transmitted according to one or more embodiments of the systems and methods of the present disclosure.
Figure 3B:
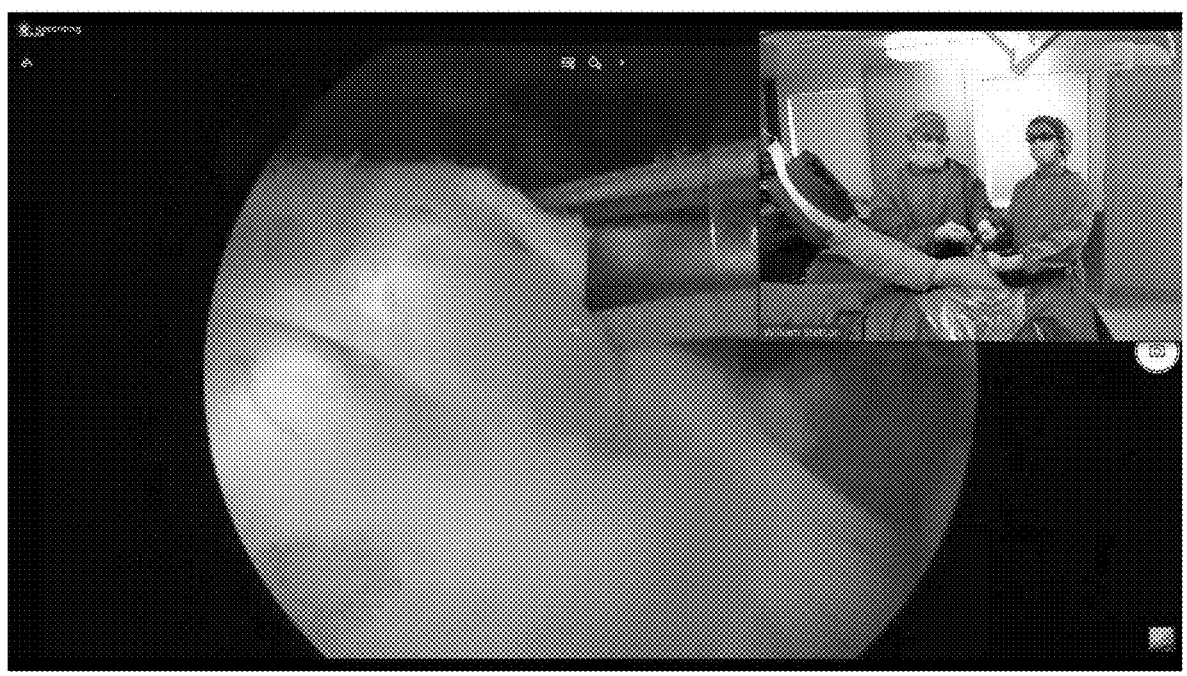

The video conferencing platform includes instructions therein, which, when executed by the processor 303 of the remote site system 300, cause the remote site system 300 to receive, via the network adapter 304, the videos with the overlaid annotations transmitted by the medical site system 200. The instructions of the video conferencing platform, when executed by the processor 303 of the remote site system 300, also cause the display of the remote site system 300 to display the videos with the overlaid annotations transmitted by the medical site system 200. FIG. 3A depicts videos with overlaid annotations (e.g., an arrow) transmitted by the medical site system and displayed on the display 301 of the remote site system 300 according to one embodiment of the present disclosure, and FIG. 3B depicts videos without overlaid annotations transmitted by the medical site system and displayed on the display 301 of the remote site system 300 according to one embodiment of the present disclosure.

In one embodiment, the video conferencing platform also includes instructions, which, when executed by the processor 205 of medical site system 200, cause the microphone 209 in the medical facility to capture audio from the medical professional performing the surgical procedure and/or other medical personnel in the medical facility (e.g., medical personnel in the operating room), and to transmit the captured audio to the remote site system 300 via the network adapter 207.

In one embodiment, the video conferencing platform also includes instructions, which, when executed by the processor 303 of remote site system 300, cause the remote site system 300 to receive, via the network adapter 304, the audio transmitted by the medical site system 200 and cause the speaker 306 at the remote site to play the audio received from the medical site system 200.

In one or more embodiments, the video conferencing platform also includes instructions, which, when executed by the processor 303 of remote site system 300, cause the microphone 307 and the video camera 305 of the remote site system 300 to capture audio and video of the one or more remote users, and to transmit, via the network adapter 304, the captured audio and video to the medical site system 200.

The input device 308 of the remote site system 300 enables a user to input annotations on the videos captured by the first and second video cameras 201 and 202 that were transmitted to the remote site system 300 by the medical site system 200. In one or more embodiments, the video conferencing platform also includes instructions, which, when executed by the processor 303 of remote site system 300, cause the remote site system 300 to transmit, via the network adapter 304, the annotations to the medical site system 200.

In the illustrated embodiment, the video conferencing platform includes instructions, which, when executed by the processor 205 of the medical site system 200, cause the medical site system 200 to receive, via the network adapter 207, the audio and video of the one or more remote users transmitted by the remote site system 300, cause the speaker 306 in the medical facility to play audio captured by the microphone 307 of the remote site system 300, cause the display 203 in the medical facility to display the video captured by the video camera 305 of the remote site system 300, and/or cause the display 203 in the medical facility to display the annotations input by the input device 308 of the remote site system 300.

Figure 2:
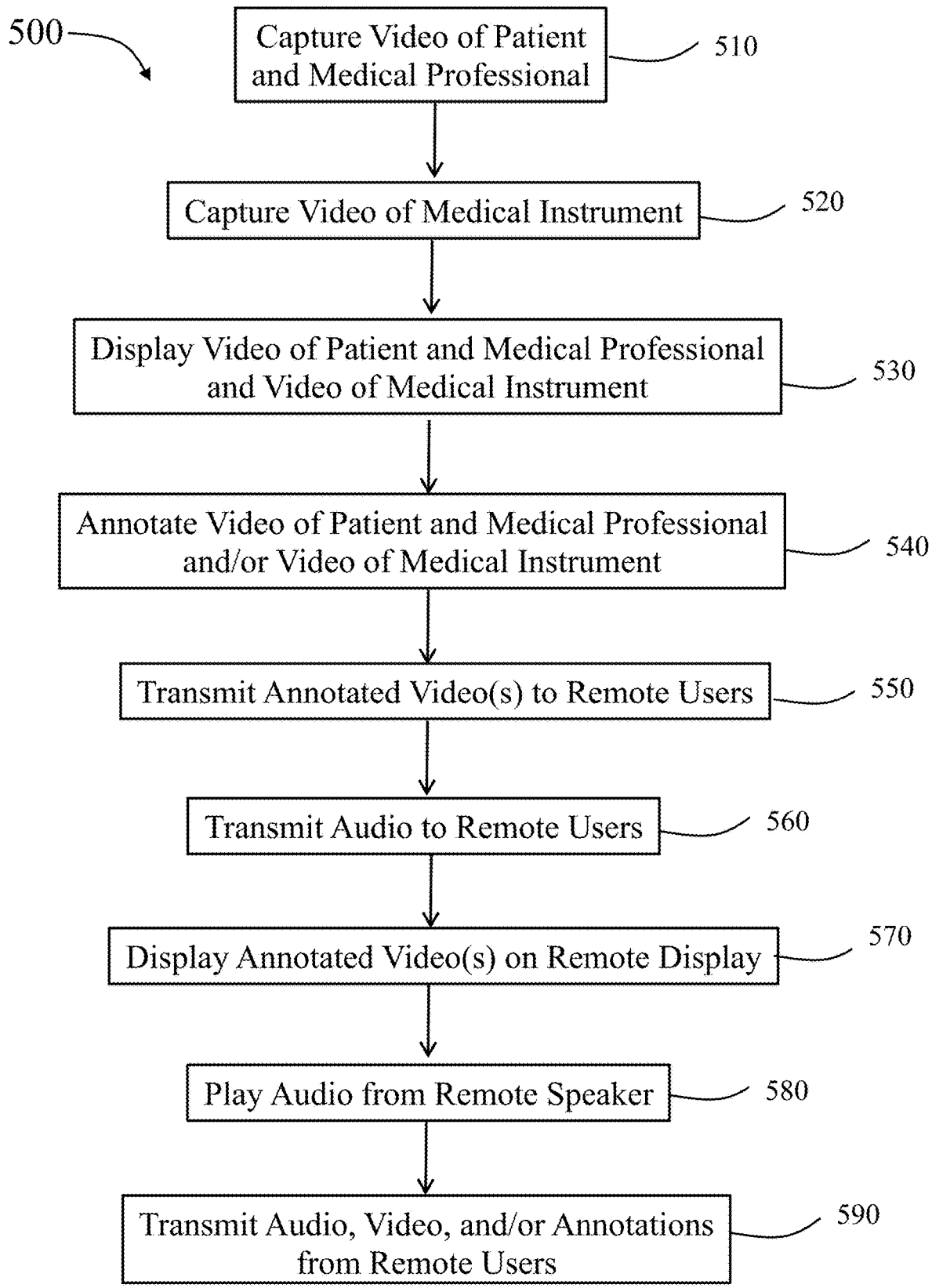
FIG. 2 is a flowchart illustrating tasks of a method of teaching a medical procedure according to one embodiment of the present disclosure.

FIG. 2 is a flowchart illustrating tasks of a method 500 of teaching a surgical procedure to one or more remotely located individuals according to one embodiment of the present disclosure. In the illustrated embodiment, the method 500 includes a task 510 of capturing a video (e.g., an extracorporeal video stream) of a patient and a medical professional (e.g., a surgeon) performing a surgical procedure on the patient with at least one surgical instrument. In one or more embodiments, the video may be captured with a first video camera located in a medical facility (e.g., an operating room).

In the illustrate embodiment, the method 500 also includes a task 520 of capturing a video of the one or more surgical instruments during performance of the surgical procedure by the medical professional on the patient. In one or more embodiments, the video may show a surgical instrument being utilized to perform a surgical operation inside the patient (e.g., arthroscopic repair of a patient's rotator cuff). That is, in one or more embodiments, the video captured in task 520 may be intracorporeal video of the patient at the site where the one or more medical instruments are being utilized by a medical professional during a medical procedure. In one or more embodiments, the video of the surgical instrument may be captured with a second video camera (e.g., a surgical video camera) inside the patient proximate to the surgical site.

In the illustrated embodiment, the method 500 also includes a task 530 of displaying the video of the medical professional and the patient captured during task 510, and displaying the video of the one or more surgical instruments being utilized in the surgical procedure captured during task 520, on one or more displays located in the medical facility (e.g., the operating room) in which the surgical procedure is being performed. In one or more embodiments, the video of the medical professional and the patient and the video of the one or more surgical instruments may be displayed in separate windows on the same display, the video of the medical professional and the patient and the video of the one or more surgical instruments may be displayed in the same window on the same display, or the video of the medical professional and the patient and the video of the one or more surgical instruments may be displayed on separate displays. In one or more embodiments, the task 530 includes displaying the video of the medical professional and the patient and the video of the one or more surgical instruments synchronously or substantially synchronously. In one or more embodiments, the video of the medical professional and the patient and the video of the one or more surgical instruments displayed in task 530 may both be displayed on the display in real-time or substantially in real-time. In one or more embodiments, the display on which the videos of the medical professional, the patient, and the surgical instrument are displayed in task 530 may be a monitor of a computer, and the computer may be electrically connected to the first video camera and the second video camera (e.g., the surgical video camera) by a video capture card of the computer.

In the illustrated embodiment, the method 500 also includes a task 540 of annotating the video of the surgical instrument and/or annotating the video of the patient and the medical professional. The task 540 of annotating the video may be performed by an individual distinct from the medical professional performing the surgical procedure on the patient (e.g., the task 540 of annotating the video may be performed by a medical assistant, such as a surgical technician, in the operating room). In one or more embodiments, the network connected computer on which videos are displayed may be operating a video conferencing platform, and the task 540 of annotating the video may be performed by an individual interfacing with the video conferencing platform. In one or more embodiments, the video conferencing platform may be stored locally on memory of the computer or the video conferencing platform may be stored on a remote server (i.e., the video conferencing server may be hosted in the "cloud") accessible by the network connected computer in the medical facility (e.g., the operating room). The annotations may include text and/or graphic symbols. For instance, the task 540 of annotating the video may include inputting text and/or symbols (e.g., an arrow or an oval) identifying various anatomical features of the patient (e.g., identifying one or more muscles, tendons, or bones of the rotator cuff, such as the head of the humerus). The task 540 of annotating the video may be performed utilizing any suitable input device, such as a mouse, a stylus, a keyboard, and/or a touchscreen (i.e., a touch sensitive display), connected to the computer in the medical facility (e.g., the operating room).

In the illustrated embodiment, the method 500 also includes a task 550 of transmitting, over a network, the video of the medical professional and the patient and the video of the surgical instrument, together with the overlaid annotations, to the one or more remote users. The task 550 of transmitting the videos and the overlaid annotations may be performed by the video capture card and a network adapter of the computer. The task of transmitting the videos and the overlaid annotations may be performed over a wired network or a wireless network depending, for instance, on the desired network reliability and/or the desired network connection speed between the medical facility and the system operated by the one or more remote users. In one or more embodiments, the task 550 of transmitting the video of the medical professional and the patient and the video of the medical instrument, together with the overlaid annotations, may be performed in real-time or substantially in real-time with the performance of the surgical procedure on the patient.

In the illustrated embodiment, the method 500 also includes a task 560 of transmitting audio from the medical professional performing the surgical procedure and/or one or more medical assistants at the medical facility (e.g., medical personnel in the operating room) to the one or more remote users. The audio transmitted during task 560 may be captured by a microphone located in the medical facility (e.g., the operating room) and the audio may be transmitted to the remote users with the network adapter of the computer in the medical facility.

In the illustrated embodiment, the method 500 also includes a task 570 of displaying the video of the patient and the medical professional and the video of the surgical instrument, together with the overlaid annotations, on a remote display (e.g., a computer monitor remote from the medical facility) that the one or more remote users can view. In one embodiment, the video of the patient and the medical professional and the video of the surgical instrument may be displayed in separate windows on the display visible to the one or more remote users.

Additionally, in the illustrated embodiment, the method includes a task 580 of playing the audio, transmitted at task 560, from a remote speaker (e.g., a computer speaker remote from the medical facility) that the one or more remote users can hear.

In the illustrated embodiment, the method 500 also includes tasks 590 of transmitting audio and video of the one or more remote users (e.g., the trainees), captured by a microphone and a video at a remote site, to the medical facility and playing the audio and the video of the one or more remote individuals via a speaker and a display in the medical facility (e.g., the operating room) in which surgical procedure is being performed. In one or more embodiments, the tasks 590 may include transmitting annotations input by an input device (e.g., a mouse, a keyboard, a stylus, and/or a touchscreen) at the remote site to the medical facility, and displaying the annotations on the display in the medical facility. In one or more embodiments, the annotations displayed in task 590 may be overlaid over the video of the medical professional and the patient and/or the video of the one or more surgical instruments, which are displayed on the display in the medical facility in task 530. In this manner, the one or more individuals (e.g., trainees) at the remote site may communicate questions or comments verbally and/or graphically to the one or more medical professionals at the medical facility in which the surgical procedure is being performed.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, and equivalents thereof.

What is claimed is:

1. A method of teaching a surgical procedure, the method comprising:
    transmitting a first video, from a first location to a second location remote from the first location, of a surgeon in an operating room performing the surgical procedure on a patient with at least one surgical instrument;
    transmitting a second video, from the first location to the second location, of the surgical instrument during the surgical procedure;
    annotating the second video with at least one annotation; and
    transmitting, from the first location to the second location, the at least one annotation overlaid on the second video, wherein the transmission of the first video, the second video, and the at least one annotation is configured to display the first video of the surgeon and the second video of the surgical instrument having the overlaid annotation adjacent to each other on a display at the second location.

2. The method of claim 1, wherein the first video is an extracorporeal video of the surgeon and at least a portion of the patient, and wherein the second video is an intracorporeal video of the surgical instrument inside the patient.

3. The method of claim 1, wherein the transmitting the first video, the transmitting the second video, and the transmitting the at least one annotation overlaid on the second video are performed by transmitting a single video stream comprising the first video, the second video, and the at least one annotation overlaid on the second video.

4. The method of claim 1, further comprising displaying the second video on a display in the operating room.

5. The method of claim 4, further comprising displaying on the display in the operating room at least one annotation transmitted from the second location.

6. The method of claim 4, wherein the annotating the second video is performed with an input device connected to the display, the input device being selected from the group of devices consisting of a mouse, a stylus, a keyboard, a touch screen, and combinations thereof.

7. The method of claim 6, wherein the at least one annotation is selected from the group of annotations consisting of a shape, a symbol, a graphic, text, and combinations thereof.

8. The method of claim 1, further comprising transmitting, from the first location to the second location, audio captured by a microphone in the operating room.

9. The method of claim 1, further comprising generating audio, from a speaker in the operating room, captured by a microphone at the second location.

10. The method of claim 1, wherein the transmitting the first video is performed synchronously with the transmitting the second video.

11. The method of claim 10, wherein the transmitting the first video and the transmitting the second video are performed in real-time.

12. The method of claim 1, wherein the annotating the second video is performed by an individual other than the surgeon.

13. A method of teaching a surgical procedure, the method comprising:
   transmitting a first video stream, captured by a first video camera in an operating room, of a surgeon performing the surgical procedure with a least one surgical instrument; and
   transmitting a second video stream, captured by a second video camera in the operating room, of the at least one surgical instrument during the surgical procedure;
   wherein the transmission of the first video stream and the second video stream is configured to display the first video of the surgeon and the second video of the at least one surgical instrument adjacent to each other on a remote display at a location remote from the operating room.

14. The method of claim 13, wherein the transmitting the first video stream and the transmitting the second video stream are performed in real-time.

15. The method of claim 13, further comprising:
   displaying, on a display in the operating room, the second video stream;
   annotating, with an input device connected to the display, the second video stream with at least one annotation; and
   transmitting the at least one annotation overlaid on the second video stream.

16. The method of claim 13, wherein the operating room and the remote display are located in the same country or different countries.

17. The method of claim 13, wherein the first video stream comprises an extracorporeal view of the surgeon and at least a portion of the patient, and wherein the second video stream comprises an intracorporeal view of the surgical instrument inside the patient.

18. A system for teaching a surgical procedure, the system comprising:
   a first video camera in operating room configured to capture extracorporeal video of a surgeon performing the surgical procedure with at least one surgical instrument in the operating room;
   a second video camera in the operating room configured to capture intracorporeal video of the at least one surgical instrument inside the patient during the surgical procedure;
   a display in the operating room configured to display at least the intracorporeal video;
   an input device connected to the display, the input device configured to generate annotations overlaid on the intracorporeal video; and
   a network adapter configured to transmit the extracorporeal video of the surgeon, the intracorporeal video of the at least one surgical instrument, and the annotations overlaid on the intracorporeal video to a site remote from the operating room, and
   wherein, when the first video, the second video, and the annotations are displayed on a display at the site remote from the operating room, the first video of the surgeon and the second video of the surgical instrument having the overlaid annotations are adjacent to each other on the display.

19. The system of claim 18, further comprising:
   a speaker connected to the network adapter in the operating room, the speaker configured to generate audio in the operating room captured from the site remote; and
   a microphone connected to the network adapter in the operating room, wherein the network adapter is configured to transmit audio captured by the microphone to the remote site.

20. The system of claim 18, wherein the input device is selected from the group of devices consisting of a mouse, a stylus, a keyboard, a touch screen, and combinations thereof.

* * * * *